United States Patent
Lodge

Patent Number: 6,016,807
Date of Patent: Jan. 25, 2000

[54] TMJ TENSIONING DEVICE

[76] Inventor: Darlene Lodge, 1203 Puxico Rd., Percy, Ill. 62272

[21] Appl. No.: 09/170,559

[22] Filed: Oct. 13, 1998

[51] Int. Cl.⁷ .................................................. A61R 5/56
[52] U.S. Cl. ........................................ 128/848; 602/902
[58] Field of Search .................................. 128/846, 848, 128/857, 858, 859–862; 602/902, 17; 2/171, 171.2

[56] References Cited

U.S. PATENT DOCUMENTS

| | | |
|---|---|---|
| 106,091 | 8/1870 | Stowe . |
| 544,062 | 8/1895 | Jacks . |
| 649,896 | 5/1900 | Baughman . |
| 688,163 | 12/1901 | Fields . |
| 904,760 | 11/1908 | Cutting . |
| 1,110,772 | 9/1914 | Gunderman . |
| 1,216,679 | 2/1917 | Foster . |
| 1,235,419 | 7/1917 | Bloomfield . |
| 1,247,222 | 11/1917 | Cauffman . |
| 1,339,865 | 5/1920 | Rothenberger . |
| 1,471,839 | 10/1923 | Epling . |
| 3,741,202 | 6/1973 | Morgan ................................ 128/76 B |
| 3,759,256 | 9/1973 | O'Malley ............................. 128/89 A |
| 4,207,881 | 6/1980 | Richter ................................ 128/89 A |
| 5,361,416 | 11/1994 | Petrie et al. ............................ 2/171.2 |
| 5,687,743 | 11/1997 | Goodwin ................................ 128/848 |
| 5,787,894 | 8/1998 | Holt ....................................... 128/848 |

*Primary Examiner*—Michael A. Brown
*Attorney, Agent, or Firm*—Grace J. Fishel

[57] ABSTRACT

A comfortable harness device for tensioning the temporomandibular joint. The harness has a plurality of pliable, but substantially non-elastic bands. A first band encircles a wearer's face and passes under the wearer's chin. A second band is attached to the first band and with the first band forms a cup for the wearer's chin that applies a posterosuperior force on the chin. A third band is attached to the first band and embraces the posterior portion of the wearer's head adjacent the wearer's temples. A fourth band at the base of the wearer's skull may be attached to the first band adjacent the wearer's chin.

6 Claims, 2 Drawing Sheets

TMJ TENSIONING DEVICE

BACKGROUND OF THE INVENTION

1. Field of the Invention

The present invention relates to a comfortable harness device for tensioning the temporomandibular joint (TMJ) in the treatment of dislocations and fractures of the jaw.

2. Brief Description of the Prior Art

Dislocations of the jaw are most often caused by a blow to the face, but occasionally they are caused by chewing large pieces of food, yawning, or even laughing. Treatment of acute dislocations is by reduction while less severe conditions may be treated by snapping the jaw back in place with the thumbs inside of the mouth. When reduction is required, a local anesthetic is injected into the lateral pterygoid and temporalis muscles which may allow the mandible to reduce spontaneously. Alternatively, or in addition, downward pressure may be applied by the physician after the patient has been given a general anesthetic or narcotic. After the dislocation has been treated, the jaw should be temporarily stabilized with a Barton bandage or the like to maintain the mandible in a reduced position. A Barton bandage is made with an elasticized tape such as an Ace bandage that is wound about the patient's head in a double figure-of-eight.

A Barton bandage is very uncomfortable to wear. The bandage has a tendency to slip and usually requires reapplication almost daily. The pressure of the elastic band may cause headaches. It may also cause the skin to breakdown under the bandage and compressive sores to form.

Because of the problems with a Barton bandage, there have been other devices proposed for use in stabilizing the jaw, many of which include a strap that passes over the wearer's forehead or includes an elastic strap that goes under the wearer's chin. These devices are also uncomfortable and not suitable, as described below, for those patients who may need to wear the bandage for the rest of their lives.

Patients who have had a stroke or who are in a coma sometimes experience repeated dislocations of the jaw brought on by uncontrolled yawning. Under these circumstances, it is necessary to permanently place the jaws in a fixed position. A Barton bandage cannot be used for this purpose as it exerts a compressive force that may cause skin breakdown and compressive sores. Hence, the usual practice is to stitch the upper and lower jaws together, leaving some slack in the thread so that a tube may be inserted between the upper and lower teeth. Sometimes the sutures are torn loose as the patient yawns and, even when they hold, they are in the way for oral hygiene, suctioning and the like.

Fractures of the mandibular condyle are also generally caused by trauma to the chin and treatment usually involves intermaxillary fixation.

BRIEF SUMMARY OF THE INVENTION

In view of the above, it is an object of the present invention to provide a comfortable harness device for tensioning the TMJ in the treatment of dislocations of the jaw and fractures. It is another object to provide a comfortable harness device for intermaxillary fixation that can be worn for an extended period of time. Other objects and features of the invention will be in part apparent and in part pointed out hereinafter.

In accordance with the invention, a harness device is provided for supporting a jaw in closed condition such that the temporomandibular joint is tensioned. The harness device has a plurality of pliable but substantially non-elastic bands, the first of which is adapted to encircle the wearer's face in a frontal plane, passing under the wearer's chin. The first band has first and second ends and a closure for adjusting the tension applied by the first band to the wearer's head. A second band is attached to the first band and with the first band forms a cup for the wearer's chin that applies a posterosuperior force on the chin.

A third band is adapted to embrace the posterior portion of the wearer's head adjacent the wearer's temples. It also has first and second ends with the ends attached to the first band adjacent the wearer's temples for adjusting the tension applied by the third band around the wearer's head.

The invention summarized above comprises the constructions hereinafter described, the scope of the invention being indicated by the subjoined claims.

BRIEF DESCRIPTION OF THE SEVERAL VIEWS OF THE DRAWING

In the accompanying drawings, in which one of various possible embodiments of the invention is illustrated, corresponding reference characters refer to corresponding parts throughout the several views of the drawings in which.

DETAILED DESCRIPTION OF THE INVENTION

Figure 1:
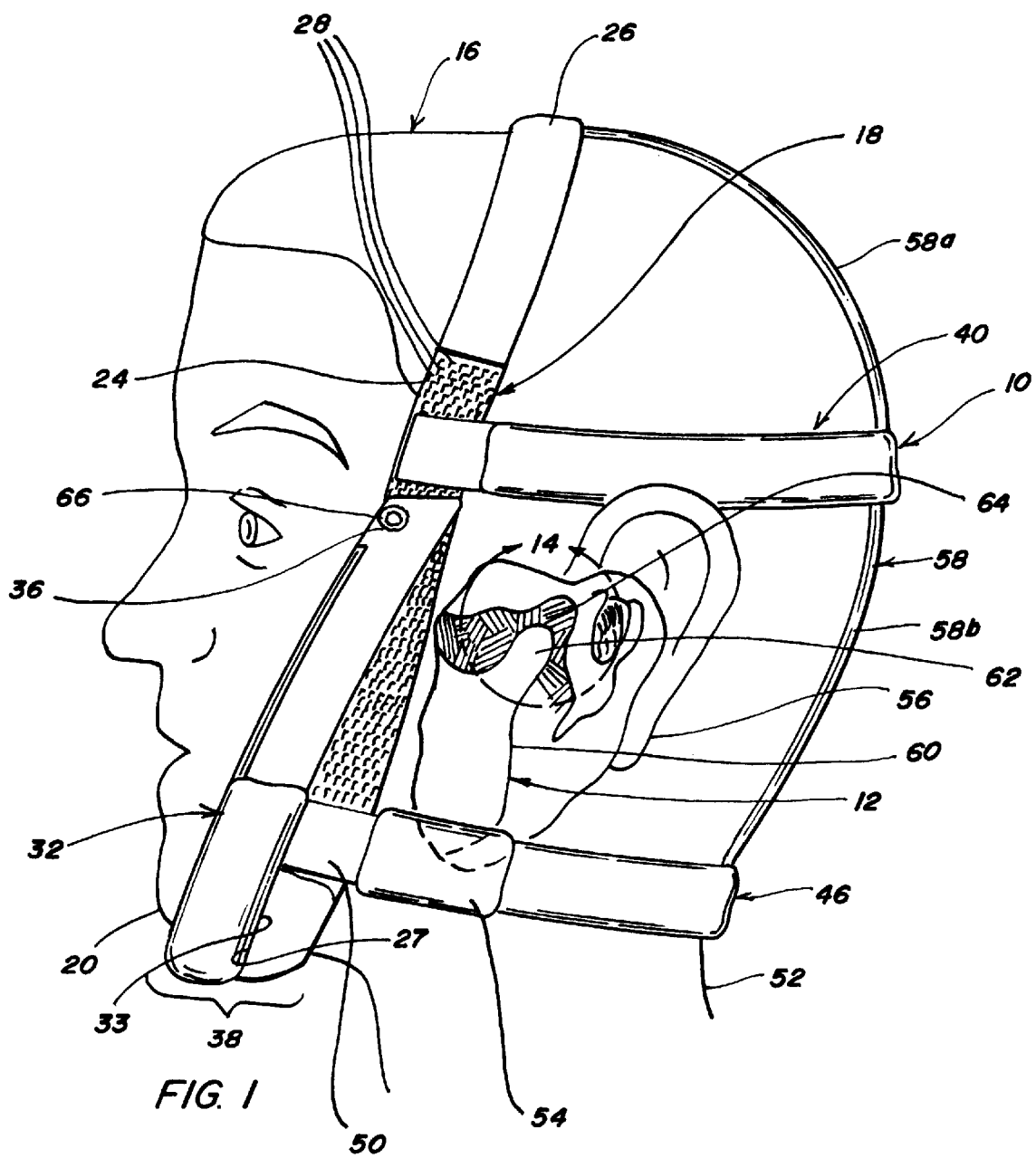
FIG. 1 is a partial sectional side view of a head showing a harness device in accordance with the present invention in use tensioning a TMJ.

Referring to the drawings more particularly by reference character, reference numeral 10 refers to a harness device for supporting a jaw 12 in closed or substantially closed condition, thus tensioning a temporomandibular joint (TMJ) 14 found on either side of a human head 16. Device 10 can be used in the treatment of a dislocated or a fractured jaw as more particularly described below.

Figure 2:
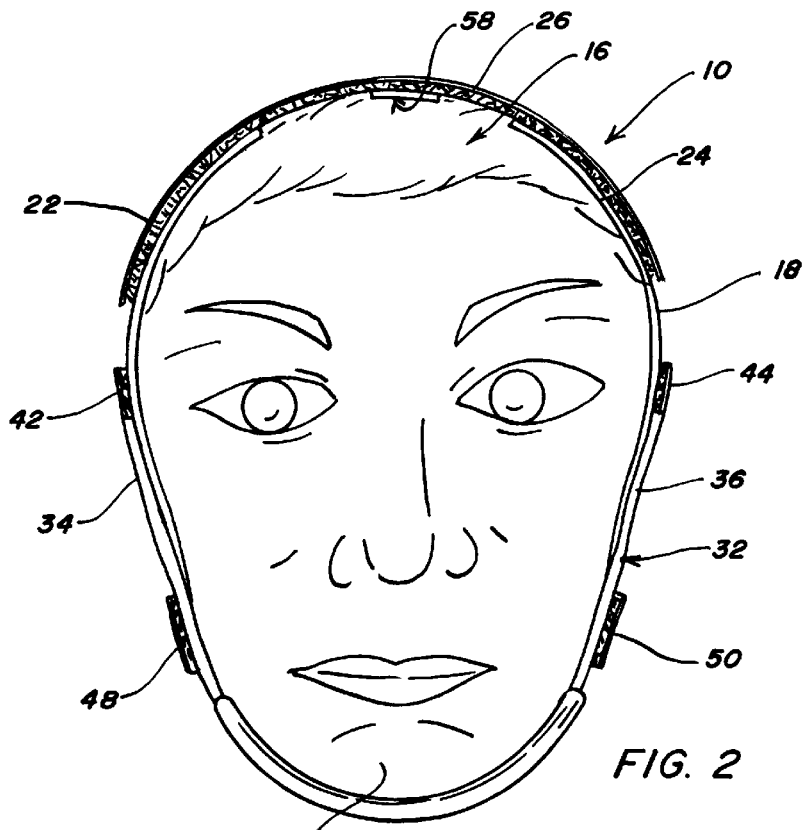
FIG. 2 is front elevational view of the harness device in use.
Figure 3:
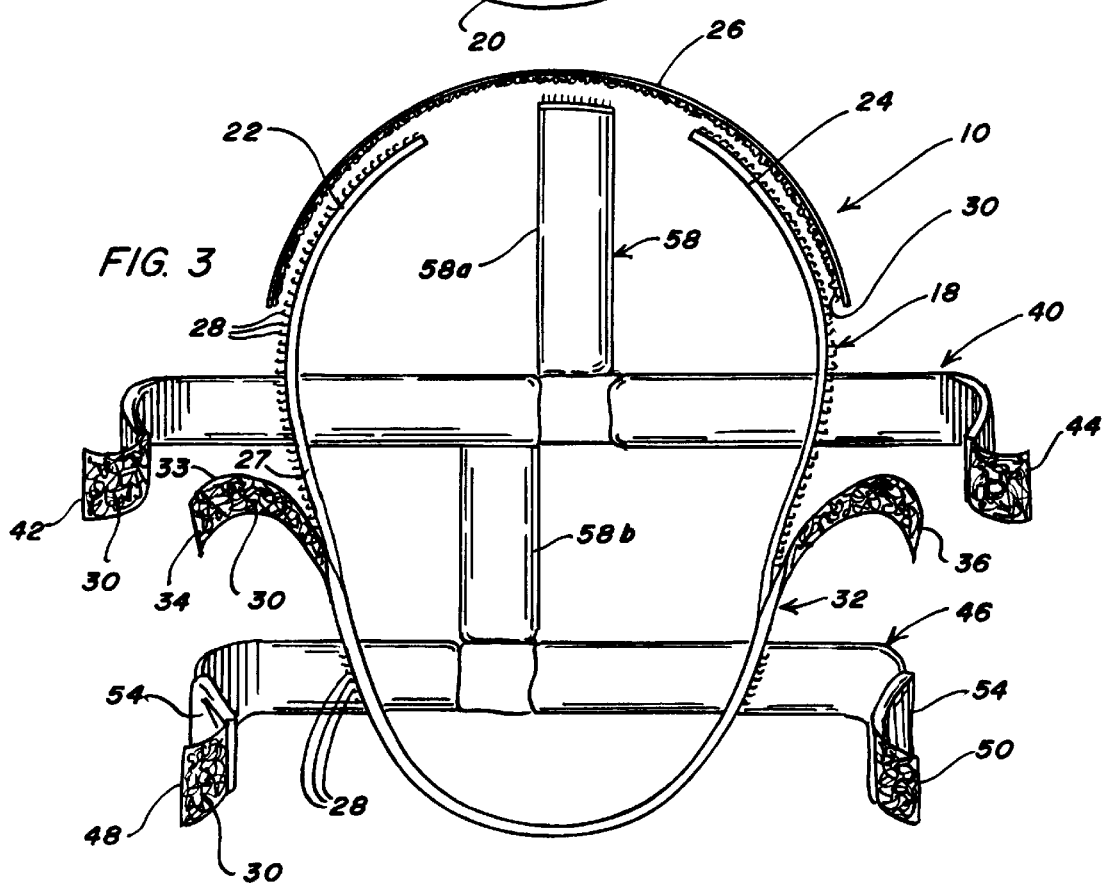
FIG. 3 is an exploded view of the harness device formed from a plurality of bands connected by a strap as more particular described below.

As best seen in FIGS. 2 and 3, device 10 is a harness formed from a plurality of interconnected bands, which while pliable are substantially non-elastic. A first band 18 is adapted to encircle wearer's head 16 in a frontal plane, passing under wearer's chin 20. First band 18 has first and second ends 22, 24, respectively and a closure 26 for adjusting the tension applied by first band 18 to the wearer's jaw 12. In the embodiment shown in the drawings, first band 18 is a strip of tape with lateral side edges 27 and with hooks 28 facing away from the wearer's face. For comfort, the inside of first band 18 touching the wearer may be covered with a soft material. Closure 26 is a strip of tape with pile 30 into which hooks 28 latch. Suitable hook and pile fasteners for this purpose are sold under the trademark VELCRO or some other name.

A second band 32 has lateral side edges 33 and first and second ends 34, 36, respectively. Second band 32 is hinged along lateral side edges 33 to lateral side edges 27 of first band 18 midway second band's length along a section of first band 18 under the wearer's chin. Second band 32 may be made of a strip of tape with pile 30 facing the wearer such that first and second ends 34, 36 can be secured at an angle to hooks 28 on first band 18, forming a cup 38 against wearer's chin 20 and applying a posterosuperior force on the wearer's chin, tensioning TMJ 14. The inside of second band 32 touching the wearer may also be covered with a soft material.

A third band 40 with first and second ends 42, 44, respectively, is provided for embracing a posterior portion of the wearer's head 16 adjacent wearer's temples. Third band 40 may be made of a strip of tape with pile 30 facing the wearer such that first and second ends 42, 44 can be secured to hooks 28 on first band 18 for adjusting the tension applied by the third band around the wearer's head. Third band 40 keeps first band 18 from slipping off wearer's head 16 and may be covered on the inside with a soft material.

A fourth band 46 with first and second ends 48, 50, respectively, is provided for embracing a posterior portion of the wearer's neck 52. As shown in the drawings, fourth band 46 may be made of a strip of tape with pile 30 facing the wearer such that first and second ends 48, 50 can be secured to hooks 28 on first band 18 adjacent cup 38 for adjusting the tension applied by fourth band 46 around the wearer's neck at the base of the skull. One function of fourth band 46 is to make it difficult for the wearer to slip device 10 off by pushing cup 38 up with his or her fingers, such as might occur in one's sleep or if the wearer is obtunded. As above, the inside of fourth band 46 touching the wearer may be covered with a soft material and a lamb's wool pad 54 may be provided under wearer's ears 56, if desired. Another important function of fourth band 46 is that it keeps harness 10 in place, even if the patient rolls his or her head from side to side on a pillow.

Cup 18 can be made more comfortable when second band 32 is hinged to first band 18 with a plurality of tack stitches. For example, five tack stitches about 1 inch apart and centered under wearer's chin 20 may be used to attach second band 32 to first band 18. When second band 32 is hinged in this manner, cup 18 conforms better to the wearer's chin 20. Cup 18 is also more comfortable if the hinge ends about ¾ inch below the point of attachment of fourth band 46 to first band 18. If connected in this manner, first band 18 does not rub under the wearer's chin.

A strap 58 is provided to interconnect first (18), third (40) and fourth (46) bands in a midsagittal plane. As shown in the drawings, strap 58 may be provided as two offset sections 58a, 58b joined to third band 40 so as to minimize the bulk under wearer's head 16. It will be understood, however, that strap 58 could be continuous. Strap 58 tends to stabilize third and fourth bands 40, 46 in a transverse plane.

While hook and pile fasteners, provided as tape 1 inch wide, are used throughout the device illustrated in the drawings, it will be understood that other closures and attachments may be used such as a pin lock, ratchet, snaps, etc. as will occur to those skilled in the fastener art. It will also be understood that the elements of the hook and pile fasteners may be reversed although the arrangement shown in the drawings is preferred as it is easier to protect the wearer from contact with hooks 28. Upholstery VELCRO is preferred for its holding strength and for comfort because the tape tends to soften with use.

FIG. 1 shows device 10 in position tensioning TMJ 14. The TMJ is defined by two primary bones, the mandibular bone 60, which articulates with the temporal bone as a ball (condyle 62) and socket (glenoid fossa 64) joint. When device 10 is placed on a patient, the operator may put a finger under first band as it is tightened. When the finger is removed, wearer's jaw 12 should come open by no more than about 1½ inches, preferably no more than about 1¼ inches. This will allow the patient to use a soda straw or even to chew small pieces of food, if his or her condition permits. It is also possible for the wearer or a nurse to clean and otherwise treat the inside of the wearer's mouth with artificial saliva or the like. Suctioning is possible and device 10 does not interfere with the attachment of an oxygen tube to the nose wherein the oxygen tube is supported by bows over the ears. Second, third and fourth bands 32, 40 and 46 should be made comfortably snug. If it is preferred that little or no movement of jaw 12 be permitted, first and second bands 18 and 32 may be applied without any provision for slack.

Device 10 has application to patients who are predisposed to jaw dislocations and offers an attractive alternative to surgical intervention. Device 10 can also be used by seizure patients to prevent tongue rolling and as a support for a fractured jaw. Other possible uses will occur to those skilled in the medical field to which the present invention is addressed. It should also be noted that device 10, as described above, is readily washable (e.g., in cold or warm water and then cold air dried).

In a preferred embodiment, alignment markings 66 (FIG. 1) may be applied to the bands once device 10 has been fitted to wearer's head 16. Wearer's hair may be washed under device 10 and a dry device applied. Alternatively, device 10 can be easily removed by undoing one end of third and fourth bands; 40 and 46 from either side of first band 18. After the bands are loosened, device 10 can be slipped off wearer's head 16 without disturbing the adjustment of the other bands. Once device 10 has been removed, it can be washed in cold or warm water and then cold air dried for reuse many times over.

In view of the above, it will be seen that the several objects of the invention are achieved and other advantageous results attained. As various changes could be made in the above constructions without departing from the scope of the invention, it is intended that all matter contained in the above description or shown in the accompanying drawings shall be interpreted as illustrative and not in a limiting sense.

What is claimed:

1. A harness device for tensioning a temporomandibular joint comprising a first band adapted to encircle a wearer's face in a frontal plane and passing under the wearer's chin, said first band having first and second ends and a closure for adjusting the tension applied by the first band to the wearer's head, a second band with first and second ends, said second band hinged to the first band along a section of the first band under the wearer's chin forming a cup for the wearer's chin, said first and second ends of the second band attached to the first band for adjusting the tension and applying a posterosuperior force on the chin, a third band adapted to embrace the posterior portion of a wearer's head adjacent the wearer's temples and having first and second ends, said ends attached to the first band adjacent the wearer's temples for adjusting the tension applied by the third band to the posterior portion of the wearer's head, and, a fourth band adapted to embrace the posterior portion of the wearer's neck at the base of his or her skull and having first and second ends, said ends attached to the first band adjacent the cup for adjusting the tension applied by the fourth band to the posterior portion of the wearer's neck, said bands being pliable but substantially non-elastic, whereby said harness device tensions the wearer's temporomandibular joints and restrains the wearer from opening his or her jaw beyond a selected extent determined by the tension applied by the first and second bands and whereby the fourth band prevents the user from removing the harness accidentally.

2. The harness device of claim 1 further comprising a strap adapted to interconnect the first, third and fourth bands in a midsagittal plane, said strap being pliable but substantially non-elastic.

3. A harness device for tensioning a temporomandibular joint comprising

- a first band having lateral side edges and adapted to encircle a wearer's face in a frontal plane and passing under the wearer's chin, said first band having first and second ends and a closure for adjusting the tension applied by the first band to the wearer's head, a second band having lateral side edges, said second band attached to the first band along the lateral side edges of said bands under a wearer's face forming a cup for the wearer's chin, said second band having first and second ends attached at an angle to the first band for conforming the cup to a wearer's face and applying a posterosuperior force on the wearer's chin,
- a third band adapted to embrace the posterior portion of a wearer's head adjacent the wearer's temples and having first and second ends, said ends attached to the first band adjacent the wearer's temples for adjusting the tension applied by the third band to the posterior portion of the wearer's head,
- a fourth band adapted to embrace the posterior portion of the wearer's neck at the base of his or her skull and having first and second ends, said ends attached to the first band adjacent the cup for adjusting the tension applied by the fourth band to the posterior portion of the wearer's neck, and
- a strap adapted to interconnect the first, third and fourth bands in a midsagittal plane,
- said bands and said strap being pliable but substantially non-elastic,
- whereby said harness device tensions the wearer's temporomandibular joints and restrains the wearer from opening his or her jaw beyond a selected extent determined by the tension applied by the first and second bands and whereby the fourth band prevents the user from removing the harness accidentally.

4. The harness of claim 3 wherein the first band has a hook fastener facing away from the wearer's face extending from at least the wearer's chin level to the first and second ends.

5. The harness of claim 4 wherein the first and second ends of the second, third and fourth bands have a pile fastener facing towards the wearer's face.

6. A method of use for a TMJ joint tensioning harness, said harness comprising a first band adapted to encircle a wearer's face in a frontal plane and passing under the wearer's chin, said first band having first and second ends and a closure for adjusting the tension applied by the first band to the wearer's head, a second band attached to the first band and with the first band forming a cup for the wearer's chin that applies a posterosuperior force on the chin, and a third band adapted to embrace the posterior portion of a wearer's head adjacent the wearer's temples and having first and second ends, said ends attached to the first band adjacent the wearer's temples for adjusting the tension applied by the third band to the posterior portion of the wearer's head, a fourth band adapted to embrace the posterior portion of the wearer's neck at the base of his or her skull and having first and second ends, said ends attached to the first band adjacent the cup for adjusting the tension applied by the fourth band to the posterior portion of the wearer's neck, said bands being pliable but substantially non-elastic, said method comprising the steps of:

(a) applying the harness to a wearer, (b) tightening the third and fourth bands around the posterior portion of the wearer's head, and (c) inserting a finger between the harness and the wearer under the wearer's chin and tightening the first and second bands with the finger under the harness and then removing the finger whereby the harness tensions the wearer's temporomandibular joints and restrains his or her jaw from opening by more than about 1½ inches.

* * * * *